United States Patent [19]

Feijen

[11] Patent Number: 5,041,292

[45] Date of Patent: Aug. 20, 1991

[54] BIODEGRADABLE HYDROGEL MATRICES FOR THE CONTROLLED RELEASE OF PHARMACOLOGICALLY ACTIVE AGENTS

[75] Inventor: Jan Feijen, Oude Grensweg, Netherlands

[73] Assignee: Theratech, Inc., Salt Lake City, Utah

[21] Appl. No.: 473,645

[22] Filed: Feb. 1, 1990

Related U.S. Application Data

[62] Division of Ser. No. 238,802, Aug. 31, 1988.

[51] Int. Cl.$^5$ .................. A61K 9/14; A61K 9/50; A61K 37/22; A61E 2/00
[52] U.S. Cl. ...................... 424/484; 424/423; 424/426; 424/488; 424/499; 424/450; 514/937
[58] Field of Search ............... 424/423, 426, 484, 488, 424/499, 450

[56] References Cited

U.S. PATENT DOCUMENTS

| | | | |
|---|---|---|---|
| 3,663,687 | 5/1972 | Evans | 424/499 |
| 4,357,259 | 11/1982 | Senyei et al. | 424/499 |
| 4,526,714 | 7/1985 | Feijen et al. | 530/395 |
| 4,670,014 | 6/1987 | Huc et al. | 604/891 |
| 4,837,381 | 6/1989 | Steber et al. | 424/502 |
| 4,849,210 | 7/1989 | Widden | 424/9 |
| 4,853,226 | 8/1989 | Machida et al. | 424/426 |
| 4,871,716 | 10/1989 | Longo et al. | 514/2 |
| 4,895,724 | 1/1990 | Cardinal et al. | 424/418 |

FOREIGN PATENT DOCUMENTS

| | | |
|---|---|---|
| 224987 | 8/1986 | European Pat. Off. |
| 261616 | 9/1987 | European Pat. Off. |
| 284569 | 3/1988 | European Pat. Off. |
| WO8801213 | 2/1988 | PCT Int'l Appl. |

OTHER PUBLICATIONS

Chemically Cross-Linked Albumin Microsphere-Davis et al., J. of Controlled Release, 4, 293-302 (1987).

Primary Examiner—Thurman K. Page
Assistant Examiner—G. S. Kishore
Attorney, Agent, or Firm—Irell & Manella

[57] ABSTRACT

A biodegradable hydrogel matrix is provided, useful for the controlled release of pharmacologically active agents. The matrix is formed by cross-linking a proteinaceous component and a polysaccharide or mucopolysaccharide, and then loading a selected drug therein. By varying temperature, ionic strength, and the composition of the hydrogel matrix, one can control degradation kinetics, the degree of uptake of a particular pharmacologically active agent, and the overall times release profile.

17 Claims, 12 Drawing Sheets

BIODEGRADABLE HYDROGEL MATRICES FOR THE CONTROLLED RELEASE OF PHARMACOLOGICALLY ACTIVE AGENTS

DESCRIPTION

1. Technical Field

This invention relates generally to drug delivery systems, and more particularly relates to biodegradable hydrogel matrices useful in the controlled release of pharmacologically active agents.

2. Background

The last decade has seen rapid development in the area of drug delivery. In particular, a number of drug delivery systems have been developed to effect the controlled release of pharmacologically active agents. For a general overview of the art, reference may be had, inter alia, to R. Baker, *Controlled Release of Biologically Active Agents*, New York: John Wiley & Sons, 1987.

One area of research has been in the use of "hydrogels", or water-swellable polymeric matrices, in drug delivery systems. See, for example, P.I. Lee, *J. Controlled Release* 2:277-288 (1985). Hydrogels are network polymers which can absorb a substantial amount of water to form elastic gels. The release of pharmacologically active agents "loaded" into such gels typically involves both absorption of water and desorption of the agent via a swelling-controlled diffusion mechanism.

A significant drawback in the use of hydrogels, however, and one that has substantially hindered the use of hydrogels in drug delivery systems, is that such formulations are generally not biodegradable. Thus, drug delivery devices formulated with hydrogels typically have to be removed after subcutaneous or intramuscular application or cannot be used at all if direct introduction into the blood stream is necessary. Thus, it would be advantageous to use hydrogels which could be degraded after application in the body without causing toxic or other adverse reactions.

Only a few types of biodegradable hydrogels have been described. These have been based on proteins (e.g., using albumin microspheres, as described in S.S. Davis et al., *J. Controlled Release* 4:293-303 (1987)) or on poly($\alpha$amino acids), as described in H.R. Dickinson et al., *J. Biomed. Mater. Res.* 15: 577-589 and 591-603 (1981)). Even these formulations, however, have proved problematic with regard to biocompatibility.

Collagen matrices, including collagen-mucopolysaccharide matrices, have been prepared and used for wound healing applications and in laminated membranes useful as synthetic skin. See, e.g., U.S. Pat. Nos. 4,060,081, 4,280,954 and 4,418,691 to Yannas et al. and 4,485,096 to Bell. These collagen matrices, however, would have limited if any utility in drug delivery as they are not "blood compatible". That is, the properties of these matrices that enable wound healing—e.g., by facilitating clotting—teach against their use in drug delivery systems.

The inventor herein has now discovered a biodegradable hydrogel which has significantly enhanced biocompatibility in that (1) blood compatibility is substantially improved, (2) immunogenicity is minimized, and (3) the hydrogel is enzymatically degraded to endogenous, nontoxic compounds. The process for making the novel hydrogel represents a further advance over the art in that, during synthesis, one can carefully control factors such as hydrophilicity, charge and degree of cross-linking. By varying the composition of the hydrogel as it is made, one can control the uptake of a particular drug, the degradation kinetics of the hydrogel formulation and the overall timed-release profile.

DISCLOSURE OF THE INVENTION

Figure 1:
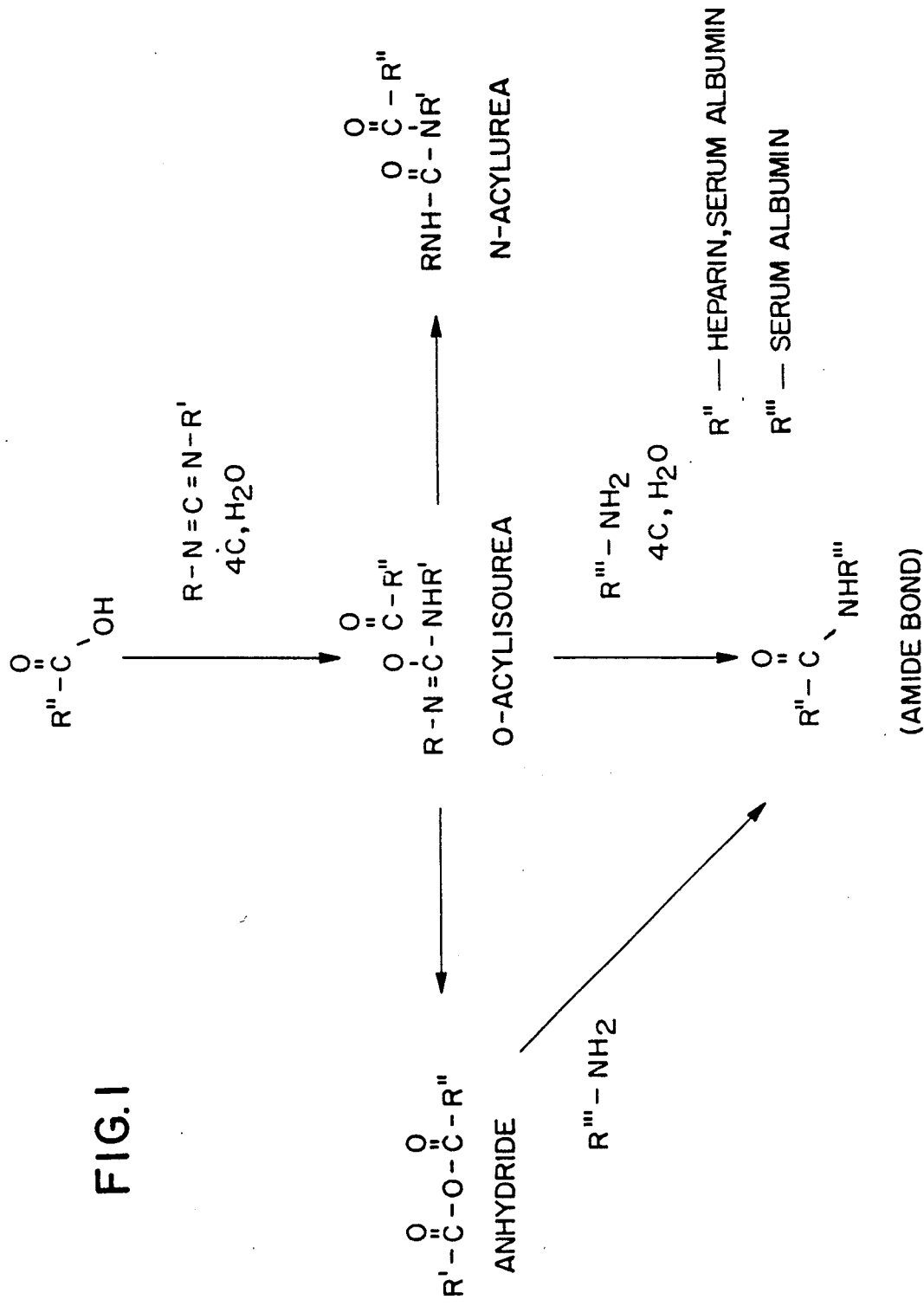
FIG. 1 schematically illustrates the preparation of a biodegradable hydrogel as described in Example 1.

A drug delivery system comprising:

(a) a biodegradable hydrogel matrix comprising a protein, a polysaccharide, and a cross-linking agent providing network linkage therebetween, wherein the weight ratio of polysaccharide to protein in the matrix is in the range of about 10:90 to 90:10; and (b) a drug contained within the matrix.

The invention also encompasses a method of making such a drug delivery system, comprising dissolving the aforementioned components in an aqueous medium, cross-linking the components to provide a three-dimensional network, and loading a selected drug, in solution or in liquid form, into the matrix. The composition of the hydrogel formed may be varied during synthesis so as to alter hydrophilicity, charge and degree of cross-linking.

As the systems of the present invention are blood- and tissue-compatible, they may be used to deliver a variety of drugs according to any number of modes of administration, e.g., oral, parenteral, or the like.

As noted above, a primary advantage of the novel hydrogels is in their enhanced biocompatibility. The use of polysaccharides or mucopolysaccharides (especially heparins) in the formulations is believed to enhance blood compatibility and significantly reduce activation of the complement system. Furthermore, as the polymeric components of the hydrogel are endogenous, the products of enzymatic degradation are endogenous as well.

MODES FOR CARRYING OUT THE INVENTION

The drug delivery systems of the present invention are formed by cross-linking a polysaccharide or a mucopolysaccharide with a protein and loading a drug, in solution or in liquid form, into the hydrogel matrices so provided. The hydrogel matrices can be prepared using different ratios of polysaccharide or mucopolysaccharide to protein and can be produced in various sizes and geometries. Upon incorporation of the selected drug as will be described, the hydrogel can be swollen to various extents depending on the composition of the gel as well as on pH, temperature, and the electrolyte concentration of the loading medium. This permits the incorporation of different types and classes of drugs, including low molecular weight drugs, peptides and proteins. After exposure of the drug-containing hydrogel to the physiological environment, i.e., to blood or tissue, drugs will be released gradually. The release rate, like the loading parameters, will depend on the composition of the gel, the degree of cross-linking, any surface treatment of the components (e.g., to increase or decrease their hydrophilicity, charge, degradation kinetics), the type of drug used, and the geometry of the hydrogel body.

By "hydrogel" as used herein is meant a water-swellable, three-dimensional network of macromolecules held together by covalent cross-links. (These covalent cross-links are sometimes referred to herein as providing a "network linkage" within the macromolecular structure.) Upon placement in an aqueous environment, these networks swell to the extent allowed by the degree of cross-linking.

By the term "pharmacologically active agent" or "drug" as used herein is meant any chemical material or compound suitable for administration which induces a desired systemic or local effect. In general, this includes therapeutic agents in all of the major therapeutic areas. By "effective" amount of a pharmacologically active agent or drug is meant a nontoxic but sufficient amount of a compound to provide the desired systemic or local effect.

By a drug or pharmacologically active agent in "liquid form", as used herein, is intended a liquid drug, i.e., neat, or a drug dissolved or dispersed in a pharmacologically compatible carrier. By drug "contained within" a hydrogel matrix is meant a drug dispersed or dissolved therein.

By "protein", as used herein, is meant both full-length proteins and polypeptide fragments, which in either case may be native, recombinantly produced, or chemically synthesized.

"Polysaccharides", as used herein, are intended to include both polysaccharides and mucopolysaccharides.

Examples of suitable polysaccharides include heparin, fractionated heparins (e.g., on an AT-III column), heparan, heparan sulfate, chondroitin sulfate, and dextran. In general, the polysaccharides or mucopolysaccharides useful in forming the hydrogels of the invention are those described in U.S. Pat. No. 4,060,081 to Yannas et al., cited supra. Heparin or heparin analogs are preferable because the compounds are strong anticoagulants and biodegradable by heparinases and amylases. In addition, using heparin or heparin analogs, i.e., compounds which are structurally related to heparin and which provide the same or similar degree of biocompatibility, appears to reduce immunogenicity and, because the compounds are highly charged, aqueous swelling is high, facilitating drug loading and release.

The protein component of the hydrogel may be, as noted above, either a full-length protein or a polypeptide fragment. It may be in native form, recombinantly produced or chemically synthesized. This protein component may also be a mixture of full-length proteins and/or fragments. Typically, the protein is selected from the group consisting of albumin, casein, fibrinogen, γ-globulin, hemoglobin, ferritin and elastin. This list is intended to be illustrative and not in any way limiting. For example, the protein component of the hydrogel may also be a synthetic polypeptide, e.g., a poly (α-amino acid) such as polyaspartic or polyglutamic acid.

Albumin is preferred as the protein component of the matrix as it is an endogenous material biodegradable in blood by proteolytic enzymes, in tissue by proteolytic enzymes associated with macrophage activity, and in different organs by phagocytosis, i.e., by the action of cells of the reticuloendothelial system (RES). Furthermore, albumin prevents adhesion of thrombocytes and is nontoxic and nonpyrogenic.

As noted above, a primary advantage of the invention lies in the fact that both the protein and polysaccharide components of the hydrogel are endogenous, biocompatible materials. This substantially reduces the likelihood of immunogenicity and, further, ensures that the products of biodegradation are also biocompatible materials.

The weight ratio of polysaccharide or mucopolysaccharide to protein within the hydrogel matrix is quite variable, and is typically within the range of about 10:90 to 90:10. More preferably, the range is about 10:90 to 60:40. The selected ratio affects drug loading, degradation kinetics, and the overall timed release profile. Thus, by varying the relative amounts of the protein and polysaccharide components in the hydrogel, one can, to a large extent, control the aforementioned factors.

In forming the novel hydrogels, one of several cross-linking methods may be used:

(1) The polysaccharide or mucopolysaccharide and the protein may be dissolved in an aqueous medium, followed by addition of an amide bond-forming cross-linking agent. A preferred cross-linking agent for this process is a carbodiimide, and a particularly preferred cross-linking agent here is the water-soluble carbodiimide N-(3-dimethyl-aminopropyl)-N-ethylcarbodiimide (EDC). In this method, the cross-linking agent is added to an aqueous solution of the polysaccharide and protein, at an acidic pH and a temperature of about 0° C. to 50° C., preferably about 4° C. to 37° C., and allowed to react for up to about 48 hrs, preferably up to about 24 hrs. The hydrogel so formed is then isolated, typically by centrifugation, and washed with a suitable solvent to remove uncoupled material.

(2) A mixture of the selected polysaccharide or mucopolysaccharide and protein is treated with a cross-linking agent having at least two aldehyde groups, thus forming Schiff-base bonds between the components. These bonds are then reduced with an appropriate reduction agent to give stable carbon-nitrogen bonds. A particularly preferred cross-linking agent in this procedure is glutaraldehyde, while a particularly preferred reduction agent is $NaCNBH_3$. The hydrogel matrix is isolated and purified as described above.

Prior to cross-linking, if desired, the polysaccharide component, e.g., heparin, can be partially de-N-sulfated via hydrolysis of $N-HSO_3$ groups to increase the number of free amine moieties available for cross-linking.

(3) The carboxylic and/or hydroxyl groups of a polysaccharide or mucopolysaccharide present in quaternary ammonium salt form—e.g., with Triton-B ™ are preactivated by treatment with carbonyldiimidazole in a nonaqueous medium, e.g., formamide. This is followed by reaction with saccharine and subsequent reaction with the protein in an aqueous medium. Reaction time and temperature are the same as in (1) above.

(4) A conjugate of a polysaccharide or a mucopolysaccharide with a protein may be prepared as described in U.S. Pat. No. 4,526,714 to Feijen et al., the disclosure of which is incorporated by reference. As described in that patent, conjugates of albumin and heparin may be prepared using EDC as the coupling agent.

The degree of cross-linking in the hydrogel, like the composition of the hydrogel itself, affects the degradation kinetics, loading, and overall timed release profile of the matrix. That is, a higher degree of cross-linking will generally result in slower degradation and release, while a lower degree of cross-linking will give faster degradation and release.

The hydrogel so formed is loaded with a selected drug by immersion in a solution containing the drug. Typically, hydrogels (albumin microspheres, for instance) are loaded by carrying out the crosslinking process in the presence of the drug. Alternatively, some hydrogels are loaded by immersion in a solution of the drug. Alternatively, some hydrogels are loaded by immersion in a solution of the drug in organic solvent(s), followed by evaporation of the organic solvent(s) after loading. The hydrogels of the present invention enable one to dispense with the use of organic solvents, and eliminate the possibility of contamination of the hydrogel with organic residues. That is, with the present method, the hydrogels may be loaded in an aqueous phase instead of in an organic solvent. With the present method, the hydrogels (microspheres) may be loaded in an aqueous phase drug solution after the hydrogel has been prepared and purified by washing.

The degree of drug loading is to a large extent dependent on the ionic strength of the aqueous system. In matrices formed from the ionically charged heparin (or analogs) and proteins, the degree of swelling increases significantly with decreasing ionic strength in the surrounding medium. Temperature may also be used to vary the degree of drug loading, as typically one will obtain a greater degree of drug loading at elevated temperatures due to higher swelling and drug solubility.

Another variable which influences the degree of drug loading is pH. Depending on the polysaccharide and protein used, changing the pH alters the degree of ionization, which will affect the swelling behavior of the gel and allow further flexibility in drug loading.

After equilibration, the loaded gels are dried in vacuo under ambient conditions, and stored.

A wide variety of drugs may be incorporated into the hydrogel matrices, including low molecular weight drugs like hormones, cytostatic agents and antibiotics, peptides and high molecular weight drugs like proteins, enzymes and anticoagulants (such as heparin). Virtually any drug may be loaded into the hydrogel matrices, providing that considerations such as surface charge, size, geometry and hydrophilicity are taken into account. For example, incorporation and release of a high molecular weight drug will typically require a hydrogel having a generally lower degree of cross-linking. The release of a charged drug will be strongly influenced by the charge and charge density available in the hydrogel, as well as by the ionic strength of the surrounding media.

The rate of drug release from the matrices can also be influenced by post-treatment of the hydrogel formulations. For example, heparin concentration at the hydrogel surface can be increased by reaction of the formulated hydrogels with activated heparin (i.e., heparin reacted with carbonyldiimidazole and saccharine) or with heparin containing one aldehyde group per molecule. A high concentration of heparin at the hydrogel surface will form an extra "barrier" for positively charged drugs at physiological pH values. Another way of accomplishing the same result is to treat the hydrogels with positively charged macromolecular compounds like protamine sulfate, polylysine, or like polymers. Still a further way of varying hydrogel permeability is to treat the surfaces with biodegradable block copolymers containing hydrophilic and hydrophobic blocks. The hydrophilic block can be a positively charged polymer like polylysine (which is able to covalently bind to the negatively charged heparin), while the hydrophobic block can be a biodegradable poly($\alpha$-amino acid) like poly(L-alanine), poly(L-leucine) or similar polymers.

It should be noted that several mechanisms are involved in the rate and extent of drug release. In the case of very high molecular weight drugs, the rate of release will be more dependent on the rate of hydrogel biodegradation. With lower molecular weight drugs, drug release will be more dominated by diffusion. In either case, depending on the hydrogel components selected, ionic exchange can also play a major role in the overall release profile. This is particularly true in applicants' preferred embodiment in which the hydrogel matrices have a substantial degree of ionic charge, e.g., matrices formed from ionically charged proteins (e.g., albumin) and heparin analogs.

The hydrogel matrices can be formed into capsules, tablets, films, microspheres, or the like. The compositions formulated using the hydrogel matrices can include conventional pharmaceutical carriers or excipients, adjuvants, etc. Matrices in the form of discs, slabs or cylinders can be used as implants, while microspheres can be applied as subcutaneous, intramuscular, intravenous or intra-arterial injectables. The size of the hydrogel bodies can be selected so as to direct ultimate placement. That is, depending on size, intravenously introduced microspheres may be physically trapped in the capillary beds of the lungs (size $>7$ $\mu$m), phagocytosed by cells of the RES system (size $>100$ nm) which will locate the particles mainly in the liver and spleen, or may become lodged at extracellular sites (size $<100$ nm).

It is to be understood that while the invention has been described in conjunction with the preferred specific embodiments thereof, that the foregoing description as well as the examples which follow are intended to illustrate and not limit the scope of the invention, which is defined by the scope of the appended claims. Other aspects, advantages and modifications within the scope of the invention will be apparent to those skilled in the art to which the invention pertains.

EXAMPLE 1

Preparation of a Biodegradable Hydrogel

Heparin (400 mg, 0.036 mmole) was added to 750 ml double distilled water. Human serum albumin ("HSA", 550 mg, 0.0085 mmole) was added to 1.0 ml double distilled water, and both solutions were kept at 4° C. to dissolve overnight. N-(3-dimethylaminopropyl)-N-ethylcarbodiimide ("EDC"), 94 mg, was then added to 250 ml double distilled water and dissolved at 4° C. The heparin solution, along with 1 ml of the albumin solution and a stir bar, was placed in a 2 ml polyethylene-polypropylene syringe of which the top had been cut off. A plunger was placed on the syringe and the solutions were thoroughly mixed. The EDC solution was added and the mixture was mixed again. All steps were carried out at 4° C.

After 24 hours, the resulting gel was removed from the syringe by swelling the syringe in toluene, and the gel was then equilibrated with phosphate buffered saline ("PBS") to remove uncoupled material.

FIG. 1 outlines the general reaction scheme for this synthesis.

EXAMPLE 2

Preparation of Cross-linked Microspheres

Figure 2:
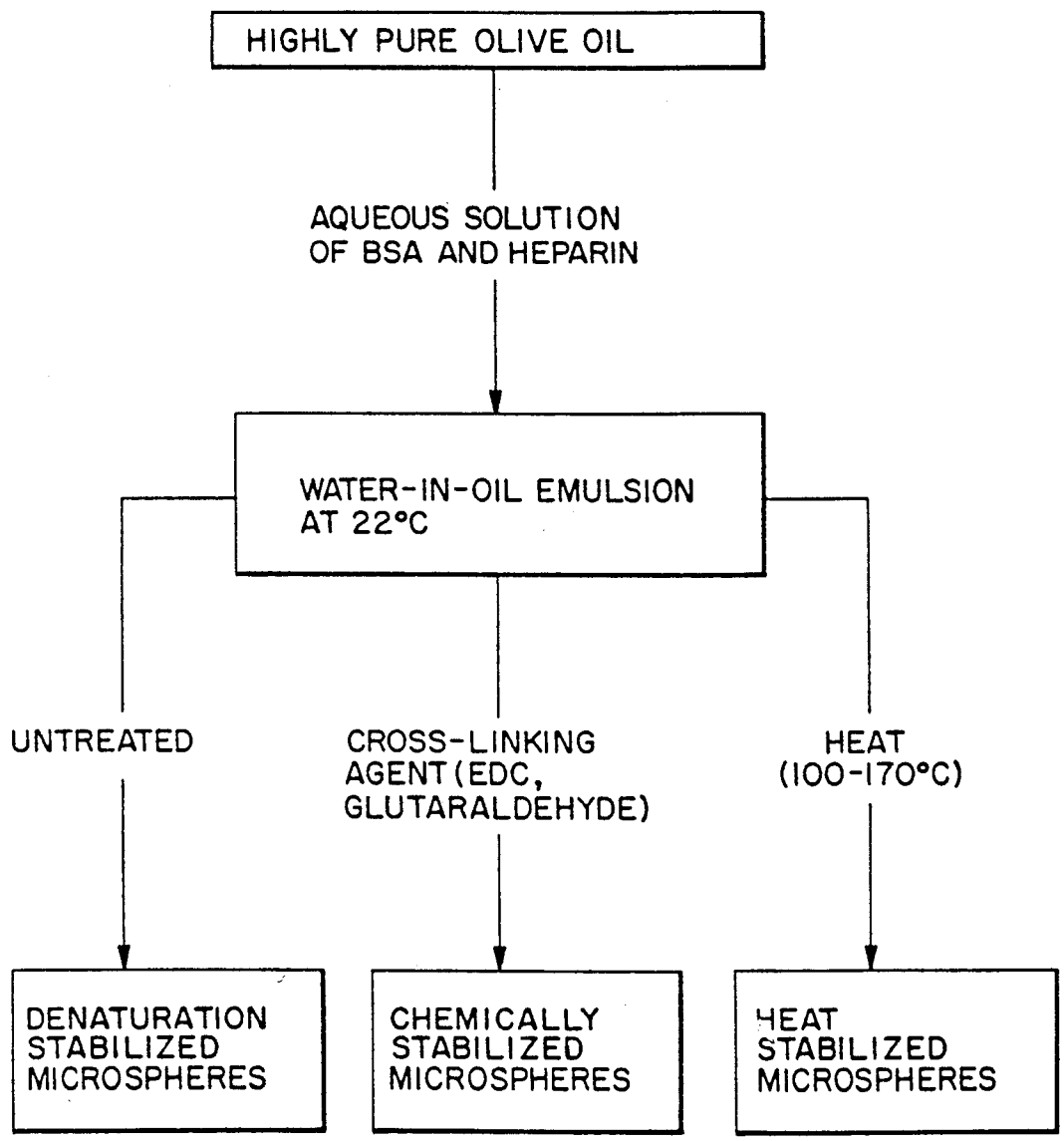
FIGS. 2 and 3 schematically illustrate the preparation of albumin-heparin microspheres as described in Example 2.

Albumin-heparin microspheres were synthesized according to the reaction scheme shown in FIG. 2. Pure olive oil (250 ml) was added to a flat-bottomed 400 ml beaker. A motor-driven double-bladed stirring bar was then submerged about two-thirds of the way into the oil. After stirring the oil for 30 minutes at 1500 rpm, 0.8 ml of an aqueous solution of albumin and heparin (~4:1, w/w) was added to the stirring oil with a 20 gauge syringe. The mixture was then stirred for 15 minutes. A solution of EDC in water (112 mgs/ml) was then added dropwise with a syringe, and the mixture was stirred overnight. The microspheres (designated "chemically stabilized" in FIG. 2) were isolated by centrifuging at 1000 rpm for 10 minutes and were subsequently vacuum filtered using a Teflon filter (pore size 0.45 microns) and washed with ether. The beads were then lyophilized and placed under vacuum overnight.

Other possibilities for obtaining the albumin-heparin microspheres are also outlined in FIG. 2. "Denaturation stabilized" microspheres are prepared as described above, except that no cross-linking agent is used. "Heat-stabilized" microspheres are also prepared in the absence of a cross-linking agent, but at a temperature of about 100–170° C., typically about 130° C.

Figure 3:
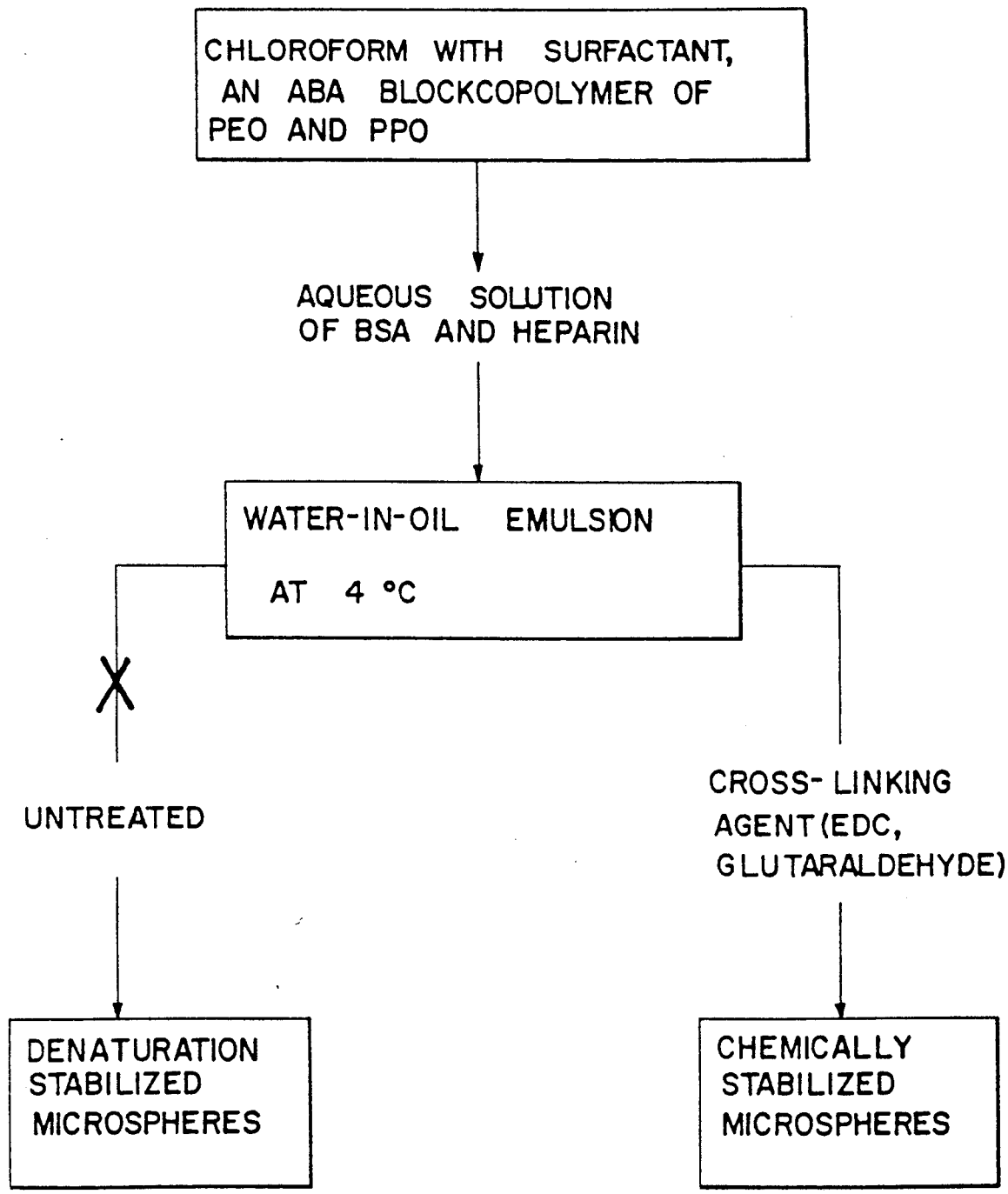

A modified synthesis scheme for preparinq albumin-heparin microspheres, using a water-in-oil emulsion, is shown in the reaction scheme of FIG. 3. In this method, 2.00 g Pluronic F-68 (a trademark of BASF Wyandotte Corp., Wyandotte, Mich., for a high molecular weight polyoxyalkylene ether) was dissolved in 8.0 ml $CHCl_3$ in a 20 ml glass scintillation vial. Albumin (100 mg) and heparin (50.0 mg) were dissolved in 500 µl water and then added to the surfactant solution to form an emulsion. An EDC solution (24.0 mg/100µl) was injected into the emulsion and the mixture was stirred overnight. Isolation of the microspheres was carried out as described previously. All steps were carried out at 4° C.

Figure 4:
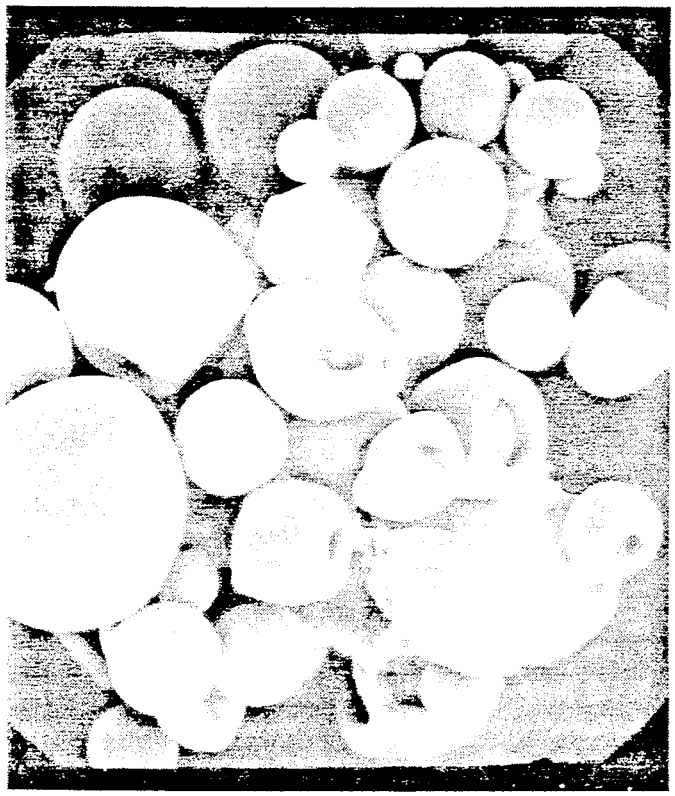
FIGS. 4 and 5 are scanning electron micrograph is of "chemically stabilized" microspheres prepared as described in Example 2.
Figure 4:
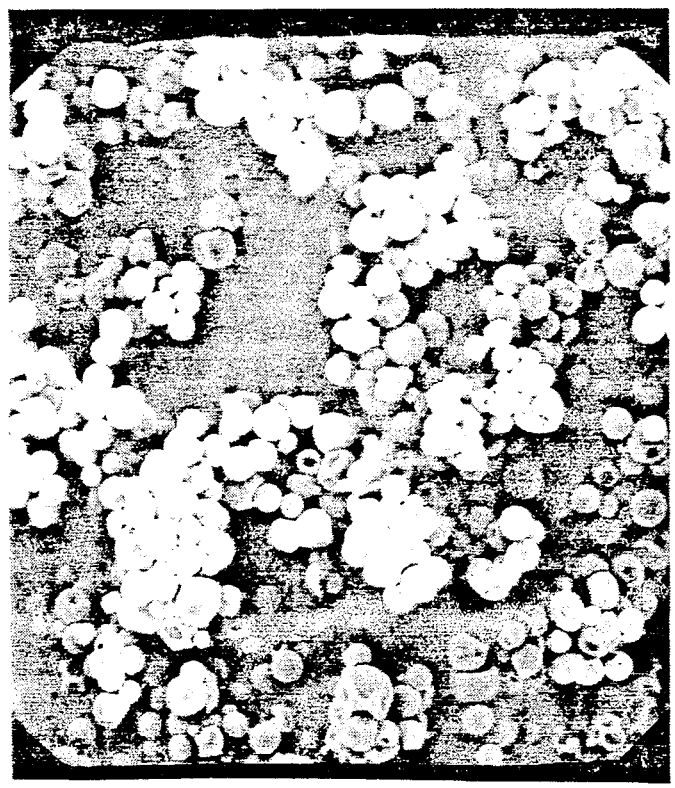
Figure 5:
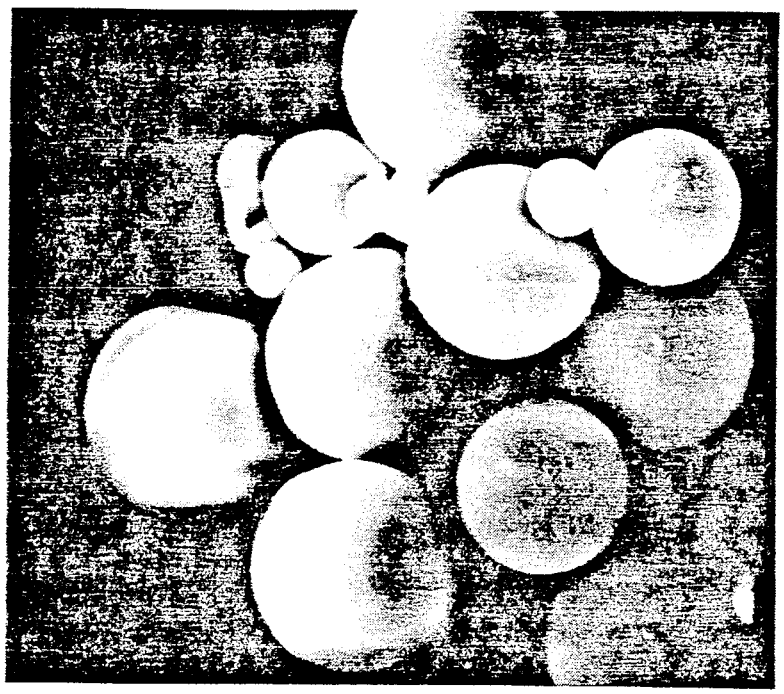
Figure 5:
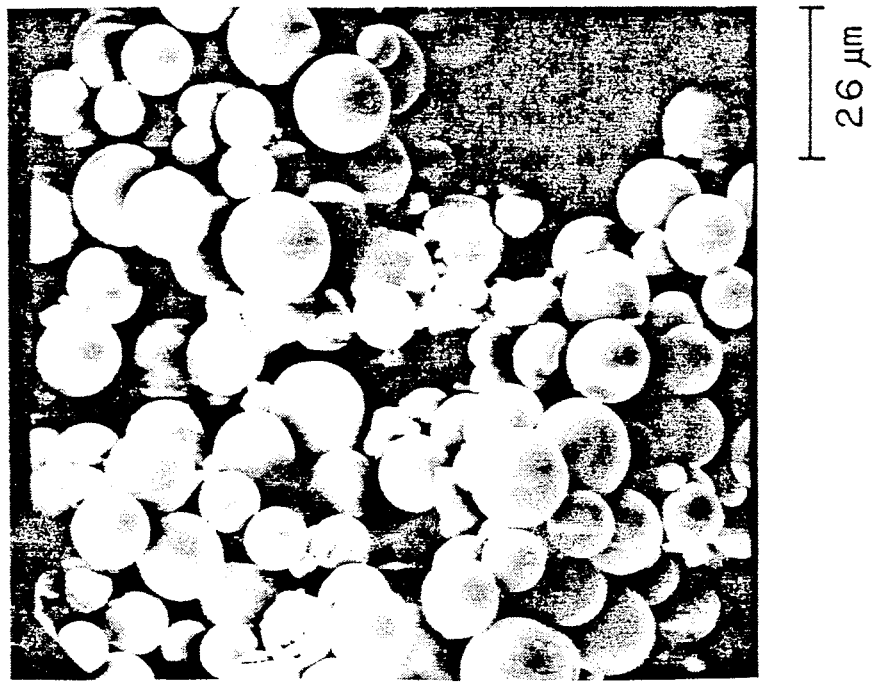

FIGS. 4 and 5 are scanning electron micrographs of albumin-heparin and albumin microspheres, respectively, which were synthesized according to the method for preparing "chemically stabilized" microspheres as outlined above. In the case of the albumin microspheres, the procedure outlined above was followed except that heparin was omitted.

EXAMPLE 3

Swelling Behavior of Albumin-Heparin Hydrogels

Figure 6:
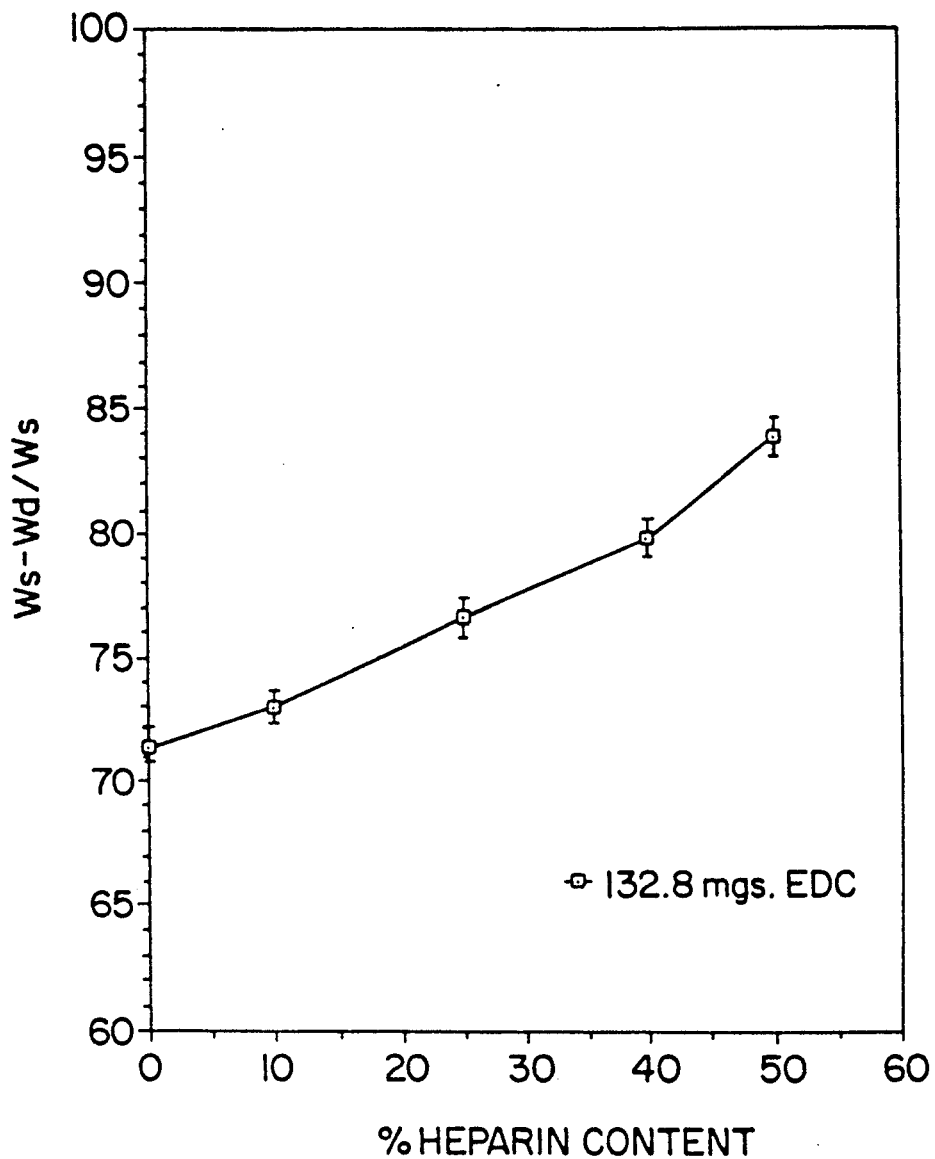
FIGS. 6 through 9 illustrate in graph form the swelling behavior of albumin-heparin microspheres in buffer solution.
Figure 7:
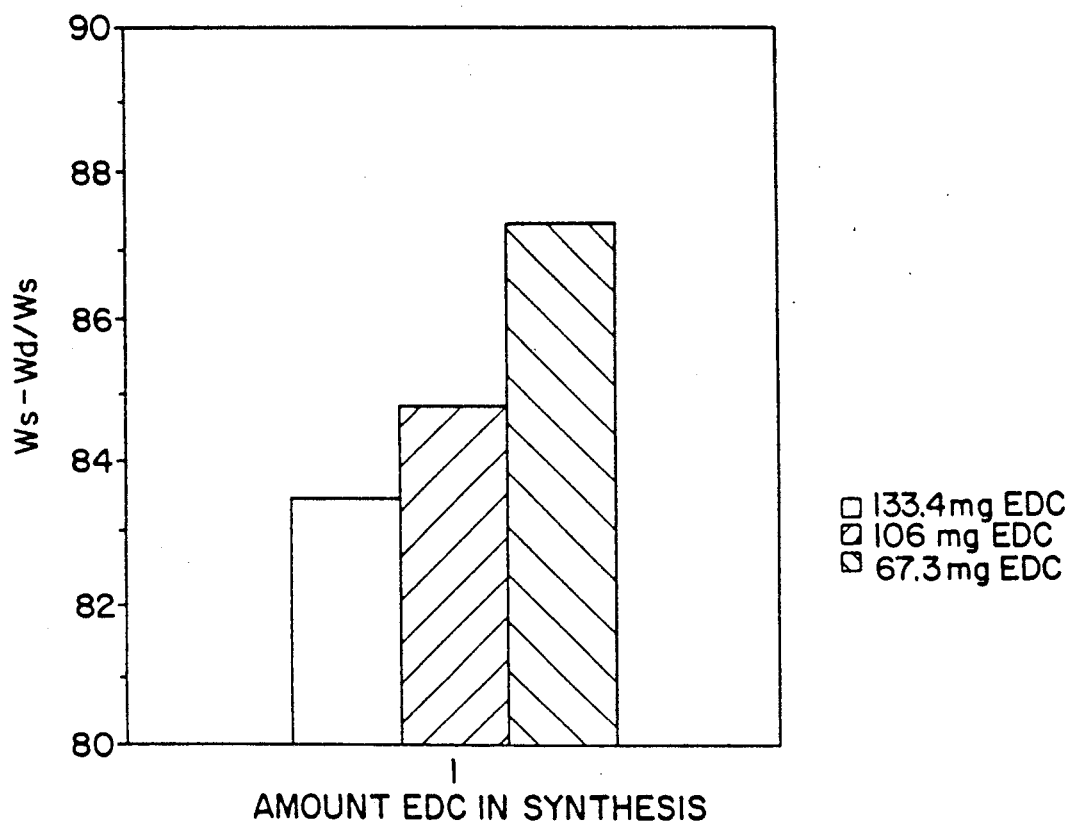
Figure 8:
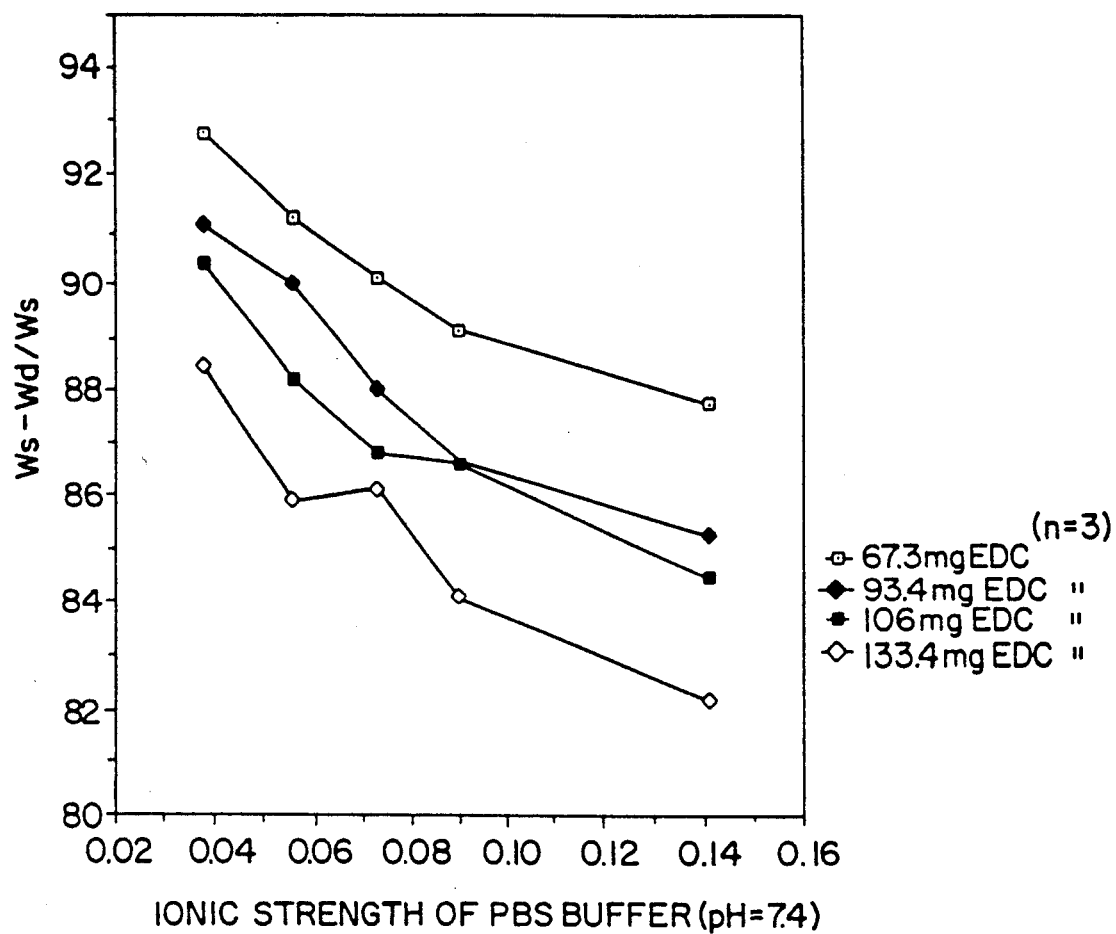
Figure 9:
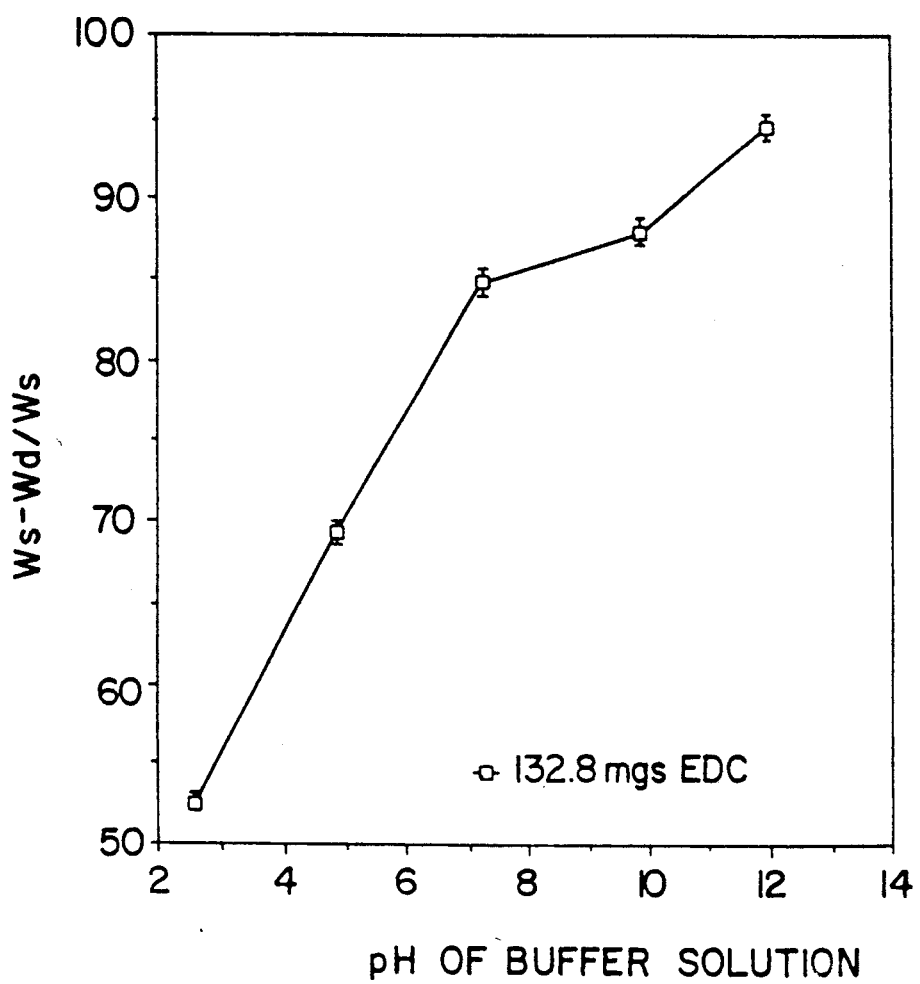

Swelling behavior of the albumin-heparin microspheres prepared as in the previous example (using varying amounts of heparin) was examined as follows.

a. The microspheres were placed in PBS buffer solution, pH 7.4, at 22° C., and the uptake of the buffer solution was monitored. As may be concluded from the graph shown in FIG. 6, uptake of the buffer solution increased with heparin content. Thus, to be able to "load" more drug into the hydrogel matrices, heparin content should be correspondingly increased.

b. Swelling studies were also carried out in PBS buffer, pH 7.4, at varying ionic strengths. Equilibrium fractions of solution in the hydrogels were obtained for hydrogels of varying cross-link density. These values are presented in FIGS. 7 and 8. In pure water, where the shielding effects of counterions in solution can't mask the fixed charges within the hydrogels, swelling occurs until the hydrogel is mechanically very weak. These figures also demonstrate that the amount of "loading" that is possible is also dependent on the amount of cross-linking agent used as well as on the ionic strength of the solvent used.

c. Further swelling studies were done to evaluate the effect of pH. As above, the studies were carried out in PBS buffer at 22° C. Here, the ionic strength of the solution was maintained at 0.15. As illustrated in FIG. 9, at low pH, the unreacted carboxylic acids (pKa about 4.2) are largely unionized, thus giving lower swelling. At higher pHs, swelling is correspondingly higher as well. This suggests that amines lose their protonation at higher pHs, thus reducing attractive electrostatic interaction.

EXAMPLE 4

In Vitro Release of a Protein from Hydrogels

Chicken egg albumin (mol. wt. - 45,000) was dissolved in 4° C. in double distilled water to make a final 10% (w/v) solution. The gels were then placed in 1 ml of these protein solutions for drug loading. When equilibrium was attained, the gels were subsequently dried at room temperature.

Figure 10:
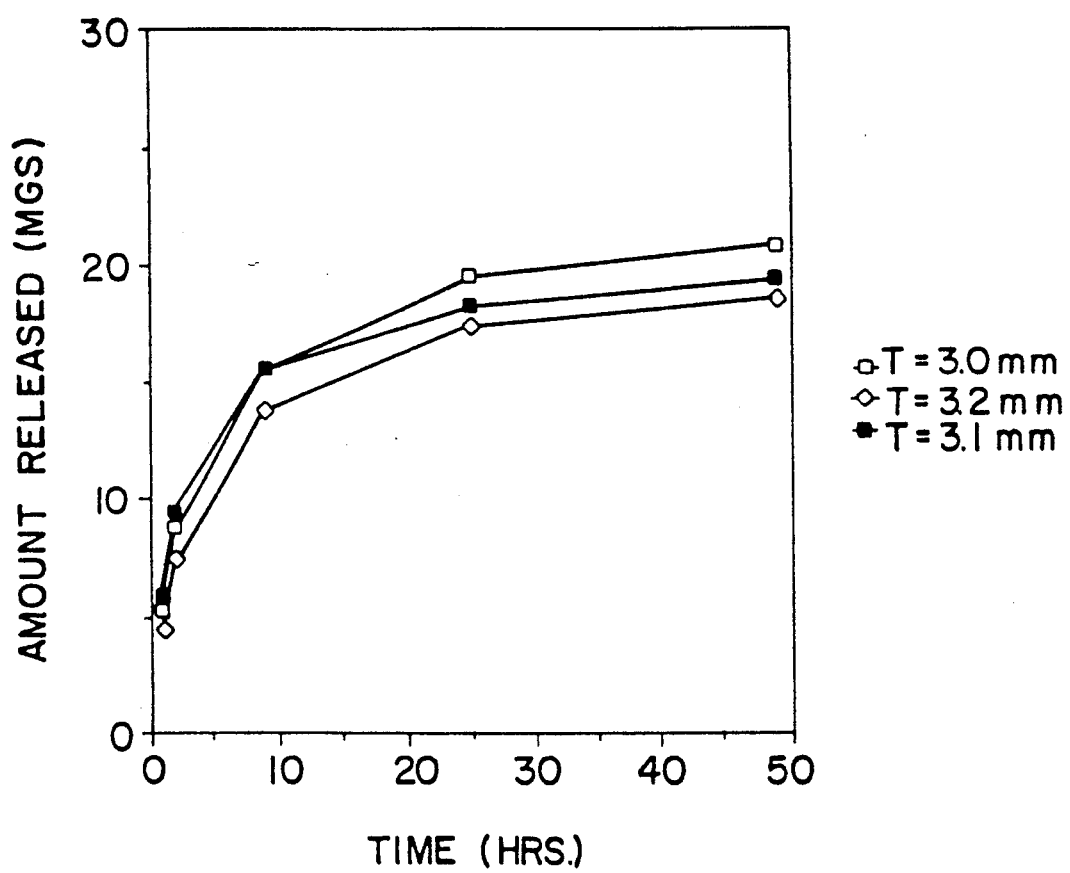
FIG. 10 illustrates in graph form the release of protein from an albumin hydrogel, as described in Example 4.

The dried protein loaded discs were then placed in 50 ml (1 disc per 50 ml) isotonic PBS buffer, pH=7.40 w/ 0.1% sodium azide at room temperature. Samples of buffer solution were withdrawn at various intervals and assayed for chicken egg albumin. Release was quantified by UV spectroscopy ($\lambda max = 279.4$ nm), and is shown in FIG. 10.

EXAMPLE 5

Effect of Composition on Macromolecular Release

The effect of albumin/heparin composition on macromolecular release was evaluated. Aqueous solutions containing either 28.6% and 17.1% albumin and heparin, respectively (i.e., a composition that is 5:3 wt./wt. albumin:heparin) or 34.3% and 11.4% albumin and heparin (i.e., a composition that is 6:2 wt./wt. albumin: heparin) were prepared. The pH was adjusted to 5.5 and the solutions cooled to 4° C. EDC was then added to both solutions to give 7.5% EDC, minimizing the exposure of the mixtures to air during EDC addition. The mixtures were then injected into film-shaped Mylar ® molds which were refrigerated at 4° C. overnight to allow in situ cross-linking of the albumin and heparin. The resultant gels were removed from the molds and discs were cut from the film with a cork bore. Final disc dimensions were 12.8 mm in diameter by 1.9 mm in thickness.

Unincorporated albumin and heparin were then exhaustively extracted in isotonic PBS containing 0.1% sodium azide until no extractable components could be detected by UV spectroscopy (for albumin) or toluidine blue assays (for heparin).

Lysozyme, a 14,400 molecular weight protein, was loaded into the albumin-heparin gels by solution sorption techniques. Hydrogel discs were immersed in 20 ml of a 0.2% lysozyme aqueous solution, pH 7.3, and equilibrated for 50 hours. The lysozyme-loaded discs were removed from the loading solutions, dried with absorbent paper to remove surface-associated lysozyme, and dried at room temperature overnight.

Figure 11:
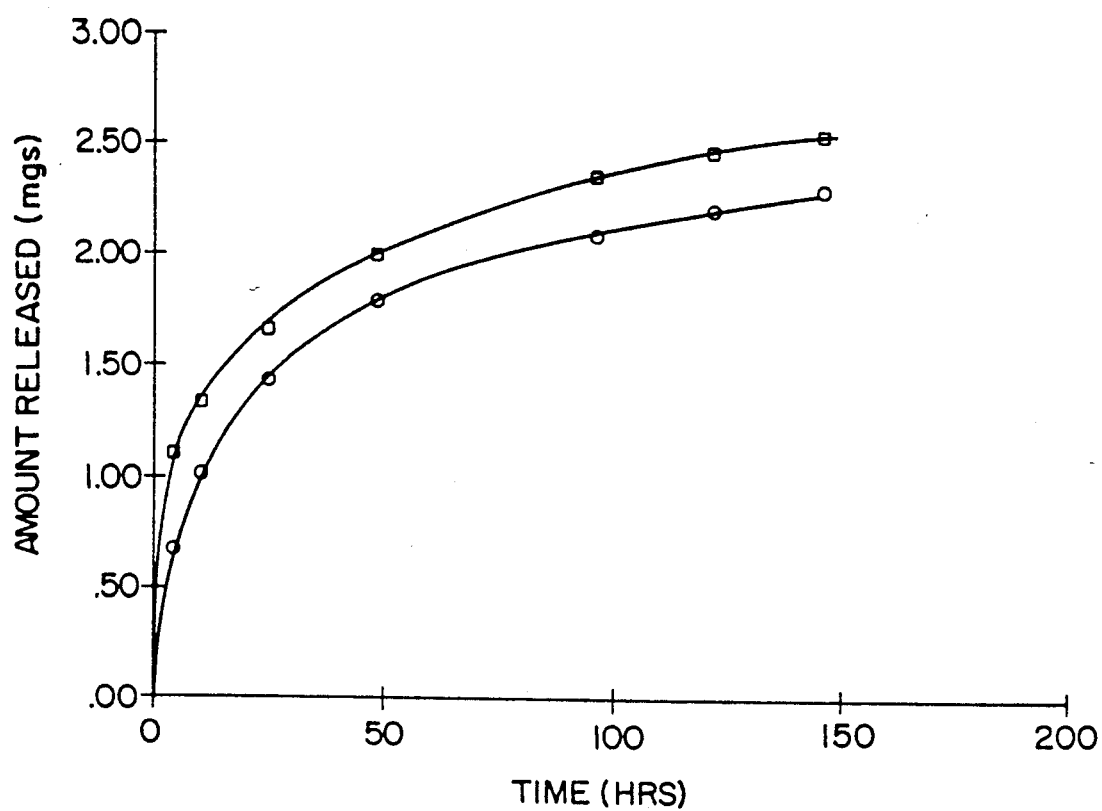
FIGS. 11 and 12 illustrate the release profile of lysozyme-loaded albumin-heparin gels as described in Example 5.
Figure 12:
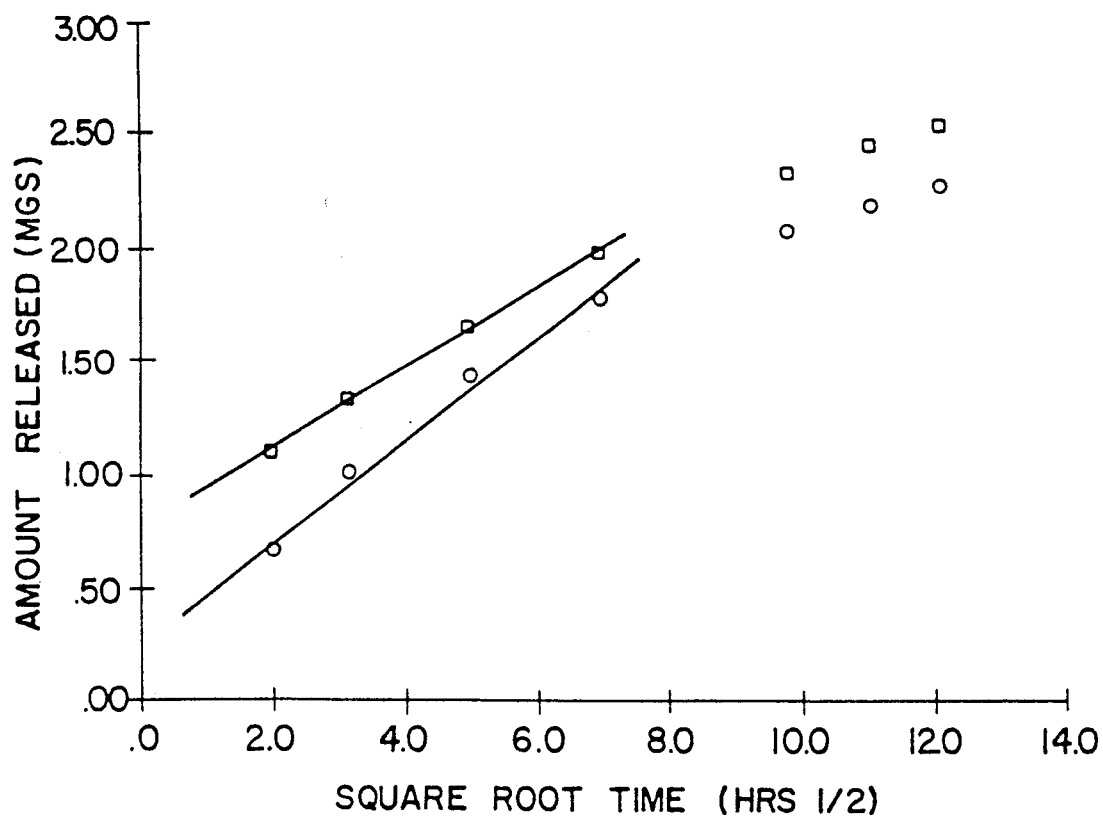

Dried lysozyme-loaded discs were first weighed and then immersed in 50 ml (1 disc per 50 ml) PBS containing 0.1% sodium azide. Samples of the PBS were withdrawn at scheduled time points for lysozyme quantitation by UV spectroscopy (280.8 mm). Lysozyme release versus time (t) and $t^{\frac{1}{2}}$ is presented in FIGS. 11 and 12, respectively. From the release data, the lysozyme diffusion coefficients were determined to be $1.82 \times 10^{-8}$ cm$^2$/sec and $9.62 \times 10^{-9}$ cm$^2$/sec for 6:2 w/w and 5:3 w/w albumin-heparin hydrogels, respectively. As expected, then, a higher percentage of heparin in the hydrogel will decrease the release rate of the trapped pharmacologically active agent, presumably through ionic exchange interactions.

What is claimed is:

1. A method of preparing microspheres useful in the controlled release of drugs, comprising:
   (a) preparing an aqueous solution of a selected protein and a polysaccharide, wherein the weight ratio of polysaccharide to protein in the solution is in the range of about 10:90 to 90:10;
   (b) admixing the protein solution with oil to provide an emulsion, wherein the volume ratio of oil to protein is in the range of about 1:1 to 500:1;
   (c) introducing a cross-linking agent into the emulsion so as to cross-link the protein and polysaccharide; and
   (d) isolating the microspheres so formed.

2. A method of preparing microspheres useful in the controlled release of drugs, comprising:
   (a) preparing an aqueous solution of a selected protein and a polysaccharide, wherein the weight ratio of polysaccharide to protein in the solution is in the range of about 10:90 to 90:10;
   (b) introducing a cross-linking agent into the solution so as to cross-link the protein and polysaccharide, and to provide a cross-linked mixture;
   (c) admixing the cross-linked mixture with oil to provide an emulsion, wherein the volume ratio of oil to protein is in the range of about 1:1 to 500:1; and 3. A method of preparing microspheres useful in the controlled release of drugs, comprising:
   preparing an aqueous solution of a selected protein and a polysaccharide, wherein the weight ratio of polysaccharide to protein in the solution is in the range of about 10:90 to 90:10;
   (b) admixing the aqueous solution with oil to provide an emulsion, wherein the volume ratio of oil to protein is in the range of about 1:1 to 500:1;
   (c) isolating the microspheres so formed; and
   (d) heating the microspheres to a temperature in the range of about 100° C. to about 170° C.

4. The method of any one of claims 1, 2 or 3, further comprising loading an effective amount of a drug into the microspheres by immersing the microspheres in a solution of the drug.

5. The method of claim 4 wherein the drug is selected from the group consisting of proteins, enzymes, mucopolysaccharides, peptides, hormones, antibodies and cytostatic agents.

6. The method of any one of claims 1, 2 or 4, wherein the polysaccharide is selected from the group consisting of heparin, heparin fragments, heparan, heparan sulfate, chondroitin sulfate, and mixtures thereof.

7. The method of claim 6, wherein the polysaccharide is selected from the group consisting of heparin, heparin fragments, heparan and heparan sulfate.

8. The method of any one of claims 1, 2 or 3, wherein the protein is selected from the group consisting of albumin, casein, fibrinogen, γ-globulin, hemoglobin, ferritin, elastin and synthetic α-amino peptides.

9. The method of claim 8 wherein the protein is albumin.

10. The method of either of claims 1 or 2, wherein the cross-linking agent is an amide bond-forming agent.

11. The method of claim 10, wherein the amide-bond forming agent is a carbodiimide.

12. The method of claim 11, wherein the carbodiimide is N-(3-dimethylaminopropyl)-N'-ethylcarbodiimide.

13. Microspheres produced by the method of claim 1.

14. Microspheres produced by the method of claim 2.

15. Microspheres produced by the method of claim 3.

16. Drug-containing microspheres produced by the method of claim 4.

17. Drug-containing microspheres produced by the method of claim 3.

* * * * *